(12) United States Patent
Parsheh et al.

(10) Patent No.: US 8,748,160 B2
(45) Date of Patent: Jun. 10, 2014

(54) BACKWARD-FACING STEP

(75) Inventors: Mehran Parsheh, Hayward, CA (US); David Rice, Albany, CA (US); Guido Radaelli, Oakland, CA (US)

(73) Assignee: Aurora Alage, Inc., Hayward, CA (US)

( * ) Notice: Subject to any disclaimer, the term of this patent is extended or adjusted under 35 U.S.C. 154(b) by 733 days.

(21) Appl. No.: 12/631,567

(22) Filed: Dec. 4, 2009

(65) Prior Publication Data

US 2011/0136212 A1    Jun. 9, 2011

(51) Int. Cl.
    *C12N 1/12*    (2006.01)
(52) U.S. Cl.
    USPC ........................ 435/257.1; 435/946
(58) Field of Classification Search
    None
    See application file for complete search history.

(56) References Cited

U.S. PATENT DOCUMENTS

| | | |
|---|---|---|
| 1,926,780 A | 9/1933 | Lippincott |
| 3,220,706 A | 11/1965 | Valdespino |
| 3,468,057 A | 9/1969 | Buisson |
| 3,897,000 A | 7/1975 | Mandt |
| 3,955,318 A | 5/1976 | Hulls |
| 4,003,337 A | 1/1977 | Moore |
| 4,115,949 A | 9/1978 | Avron et al. |
| 4,217,728 A | 8/1980 | Shimamatsu et al. |
| 4,267,038 A | 5/1981 | Thompson |
| 4,365,938 A | 12/1982 | Warinner |
| 4,535,060 A | 8/1985 | Comai |
| 4,658,757 A | 4/1987 | Cook |
| 4,813,611 A | 3/1989 | Fontana |
| 5,105,085 A | 4/1992 | McGuire et al. |
| 5,130,242 A | 7/1992 | Barclay |
| 5,227,360 A | 7/1993 | Sherba et al. |
| 5,338,673 A | 8/1994 | Thepenier et al. |
| 5,353,745 A | 10/1994 | Fahs, II |
| 5,478,208 A | 12/1995 | Kasai et al. |
| 5,518,990 A | 5/1996 | Ushio et al. |
| 5,527,456 A | 6/1996 | Jensen |
| 5,539,133 A | 7/1996 | Kohn et al. |
| 5,564,630 A | 10/1996 | Giles et al. |
| 5,573,669 A | 11/1996 | Jensen |
| 5,658,076 A | 8/1997 | Crump et al. |
| 5,658,767 A | 8/1997 | Kyle |
| 5,823,781 A | 10/1998 | Hitchcock et al. |
| 5,871,952 A | 2/1999 | Ghirardi et al. |
| 6,000,551 A | 12/1999 | Kanel et al. |
| 6,117,313 A | 9/2000 | Goldman |
| 6,166,231 A | 12/2000 | Hoeksema |
| 6,372,460 B1 | 4/2002 | Gladue et al. |
| 6,447,681 B1 | 9/2002 | Carlberg et al. |
| 6,524,486 B2 | 2/2003 | Borodyanski |
| 6,579,714 B1 | 6/2003 | Hirabayashi et al. |
| 6,626,738 B1 | 9/2003 | Shank |
| 6,736,572 B2 | 5/2004 | Geraghty |
| 6,750,048 B2 | 6/2004 | Ruecker et al. |
| 6,831,040 B1 | 12/2004 | Unkefer et al. |
| 6,871,195 B2 | 3/2005 | Ryan et al. |
| 6,896,804 B2 | 5/2005 | Haerther et al. |
| 6,944,013 B2 | 9/2005 | Yang |
| 7,381,326 B2 | 6/2008 | Haddas |
| 7,391,608 B2 | 6/2008 | Tsai |
| 7,669,780 B2 | 3/2010 | Sugano et al. |
| 7,682,821 B2 | 3/2010 | Woods et al. |
| 7,748,650 B1 | 7/2010 | Sloan |
| 7,770,322 B2 | 8/2010 | Huntley et al. |
| 2002/0105855 A1 | 8/2002 | Behnke et al. |
| 2003/0038566 A1 | 2/2003 | Qiu |
| 2003/0116502 A1 | 6/2003 | Debusk et al. |
| 2003/0140021 A1 | 7/2003 | Ryan et al. |
| 2003/0199490 A1 | 10/2003 | Antoni-Zimmermann et al. |
| 2004/0121447 A1 | 6/2004 | Fournier |
| 2004/0161364 A1 | 8/2004 | Carlson |
| 2004/0262219 A1 | 12/2004 | Jensen |
| 2005/0064577 A1 | 3/2005 | Berzin |
| 2005/0095569 A1 | 5/2005 | Franklin |
| 2005/0164192 A1 | 7/2005 | Graham et al. |
| 2005/0170479 A1 | 8/2005 | Weaver et al. |
| 2005/0181345 A1 | 8/2005 | Bradbury et al. |
| 2005/0260553 A1 | 11/2005 | Berzin |
| 2005/0273885 A1 | 12/2005 | Singh et al. |
| 2006/0031087 A1 | 2/2006 | Fox |
| 2006/0044259 A1 | 3/2006 | Hotelling et al. |
| 2006/0045750 A1 | 3/2006 | Stiles |
| 2006/0122410 A1 | 6/2006 | Fichtali |
| 2006/0155558 A1 | 7/2006 | Corpening |
| 2006/0166243 A1 | 7/2006 | Su et al. |

(Continued)

FOREIGN PATENT DOCUMENTS

| | | |
|---|---|---|
| WO | WO2004106238 A2 | 12/2004 |
| WO | WO2009037683 A1 | 3/2009 |

(Continued)

OTHER PUBLICATIONS

Santin-Montanaya, I. Optimal growth of *Dunaliella primolecta* in axenic conditions to assay herbicides, Chemosphere, 66, Elsevier 2006, pp. 1315-1322.

Felix, R. Use of the cell wall-less alga *Dunaliella bioculata* in herbicide screening tests, Annals of Applied Biology, 113, 1988, pp. 55-60.

Janssen, M. Photosynthetic efficiency of *Dunaliella tertiolecta* under short light/dark cycles, Enzyme and Microbial Technology, 29, 2001, pp. 298-305.

Saenz, M.E. Effects of Technical Grade and a Commercial Formulation of Glyphosate on Algal Population Growth, Bulletin of Environmental Contamination Toxicology, 1997, pp. 638-644.

Polle et al., "tla1, a DNA insertional transformant of the green alga *Chlamydomonas reinhardtii* with a truncated light-harvesting chlorophyll antenna size," Planta, vol. 217, No. 1, May 2003, pp. 49-59.

(Continued)

*Primary Examiner* — Debbie K Ware
(74) *Attorney, Agent, or Firm* — Carr & Ferrell LLP (57) ABSTRACT

Systems, methods and media for carbonation of fluid in an algae cultivation pond via the use of backward-facing steps are disclosed. In a first aspect, a method for initiating carbonation of a fluid flow in an algae cultivation pond is disclosed. Fluid flow is initiated over a backward-facing step in the algae cultivation pond. A backflow region is generated in the fluid flow downstream of the backward-facing step. Carbon dioxide is provided to the backflow region.

6 Claims, 8 Drawing Sheets

(56) References Cited

U.S. PATENT DOCUMENTS

| | | |
|---|---|---|
| 2006/0192690 A1 | 8/2006 | Philipp |
| 2007/0115626 A1 | 5/2007 | Peng et al. |
| 2007/0155006 A1 | 7/2007 | Levin |
| 2007/0289206 A1 | 12/2007 | Kertz |
| 2008/0118964 A1 | 5/2008 | Huntley et al. |
| 2008/0120749 A1 | 5/2008 | Melis et al. |
| 2008/0155888 A1 | 7/2008 | Vick et al. |
| 2008/0155890 A1 | 7/2008 | Oyler |
| 2008/0160488 A1 | 7/2008 | Younkes et al. |
| 2008/0160591 A1 | 7/2008 | Willson et al. |
| 2008/0160593 A1 | 7/2008 | Oyler |
| 2008/0220486 A1 | 9/2008 | Weiss |
| 2008/0293132 A1 | 11/2008 | Goldman et al. |
| 2009/0011492 A1 | 1/2009 | Berzin |
| 2009/0029445 A1 | 1/2009 | Eckelberry et al. |
| 2009/0061928 A1 | 3/2009 | Lee et al. |
| 2009/0126265 A1 | 5/2009 | Rasmussen et al. |
| 2009/0137031 A1 | 5/2009 | Hirabayashi |
| 2009/0148931 A1 | 6/2009 | Wilkerson et al. |
| 2009/0151241 A1 | 6/2009 | Dressler et al. |
| 2009/0162919 A1 | 6/2009 | Radaelli et al. |
| 2009/0186860 A1 | 7/2009 | Huff et al. |
| 2009/0234146 A1 | 9/2009 | Cooney et al. |
| 2009/0319338 A1 | 12/2009 | Parks et al. |
| 2009/0325270 A1 | 12/2009 | Vick et al. |
| 2010/0068772 A1 | 3/2010 | Downey |
| 2010/0100520 A1 | 4/2010 | Dargue et al. |
| 2010/0170149 A1 | 7/2010 | Keeler et al. |
| 2010/0170150 A1 | 7/2010 | Walsh, Jr. |
| 2010/0183744 A1 | 7/2010 | Weissman et al. |
| 2010/0196995 A1 | 8/2010 | Weissman et al. |
| 2010/0198659 A1 | 8/2010 | Meltzer et al. |
| 2010/0210003 A1 | 8/2010 | King |
| 2010/0257781 A1 | 10/2010 | Batty et al. |
| 2010/0260618 A1 | 10/2010 | Parsheh et al. |
| 2010/0261922 A1 | 10/2010 | Fleischer et al. |
| 2010/0314324 A1 | 12/2010 | Rice et al. |
| 2010/0323387 A1 | 12/2010 | Bailey et al. |
| 2010/0325948 A1 | 12/2010 | Parsheh et al. |
| 2010/0327077 A1 | 12/2010 | Parsheh et al. |
| 2011/0016773 A1 | 1/2011 | Nichols et al. |
| 2011/0023360 A1 | 2/2011 | Ryan et al. |
| 2011/0051354 A1 | 3/2011 | Fan et al. |
| 2011/0136212 A1 | 6/2011 | Parsheh et al. |
| 2011/0197306 A1 | 8/2011 | Bailey et al. |
| 2011/0258915 A1 | 10/2011 | Subhadra |
| 2011/0287531 A1 | 11/2011 | Hazlebeck |
| 2011/0287544 A1 | 11/2011 | Berzin et al. |
| 2012/0252104 A1 | 10/2012 | Waibel et al. |

FOREIGN PATENT DOCUMENTS

| | | | |
|---|---|---|---|
| WO | WO2009149519 A1 | 12/2009 | |
| WO | WO2010008490 A1 | 1/2010 | |
| WO | WO2010011335 A1 | 1/2010 | |
| WO | WO2010129041 A1 | 11/2010 | |
| WO | WO2010147648 A1 | 12/2010 | |
| WO | WO2011002487 A1 | 1/2011 | |

OTHER PUBLICATIONS

Lawrence et al., "Variation in Plants Regenerated from Vacuolate and Evacuolate Protoplasts," Plant Science, vol. 50, No. 2, 1987, pp. 125-132.

Beckmann et al., "Improvement of light to biomass conversion by de-regulation of light-harvesting protein translation in *Chlamydomonas reinhardtii*," Journal of Biotechnology, vol. 142, No. 1, 2009, pp. 70-77.

International Search Report and Written Opinion of the International Searching Authority mailed Aug. 16, 2012 for Application No. PCT/US2012/041425, filed Jun. 7, 2012.

European Search Report mailed Oct. 5, 2012 in European Patent Application No. 10772376.9, filed May 4, 2010.

Christy et al., "Effects of Glyphosate on Growth of *Chlorella*," Weed Science, vol. 29, Issue 1, Jan. 1981, pp. 5-7.

Roessler et al., "Genetic Engineering Approaches for Enhanced Production of Biodiesel Fuel from Microalgae," ACS Symposium Series; American Chemical Society, 1994, pp. 255-270.

Grima et al. "Recovery of Microalgal Biomass in Metabolites: Process Options and Economics," Biotechnology Advances 20, 2003, pp. 491-515.

Knuckey et al. "Production of Microalgal Concentrates by Flocculation and their Assessment as Aquaculture Feeds," Aquaculture Engineering 35, 2006, pp. 300-313.

Applying [online] retrieved from: http://www.merriam-webster.com/dictionary/applying, on May 21, 2011; 3 pages.

Cohen, "Chemicals from MicroAlgae", 1999, CRC Press, pp. 49 and 51.

Kureshy et al., "Effect of Ozone Treatment on Cultures of *Nannochloropsis oculata, Isochrysis galbana*, and *Chaetoceros gracilis*," Journal of the World Aquaculture Society, 1999, 30(4), pp. 473-480.

Liao et al. "An Overview of Live Feeds Production System Design in Taiwan," Rotifer and Microalgae Culture Systems, Proceedings of a US-Asia Workshop, Honolulu, HI, 1991, pp. 135-150.

Kanematsu et al., "Methods to Repress the Growth of a *Nannochloropsis*-Grazing Microflagellate," Nippon Suisan Gakkaishi 55, 1989, pp. 1349-1352 (English Translation).

Csogor et al., "Light Distribution in a Novel Photobioreactor—Modelling for Optimization," Journal of Applied Phycology, vol. 13, pp. 325-333, 2001.

Janssen et al., "Enclosed Outdoor Photobioreactors: Light Regime, Photosynthetic Efficiency, Scale-Up, and Future Prospects," Biotechnology and Bioengineering, vol. 81, No. 2, pp. 193-210, Jan. 2003.

Zittelli et al., "Mass Cultivation of *Nannochloropsis* Sp. In Annular Reactors," Journal of Applied Phycology, vol. 15, pp. 107-113, Mar. 2003.

Strzepek et al., "Photosynthetic Architecture Differs in Coastal and Oceanic Diatoms," Nature, vol. 431, pp. 689-692, Oct. 2004.

Lee et al., "Isolation and Characterization of a Xanthophyll Aberrant Mutant of the Green Alga *Nannochloropsis oculata*," Marine Biotechnology, 2006, vol. 8, pp. 238-245.

NCBI entry EE109892 (Jul. 2006) [Retrieved from the Internet on Oct. 19, 2009, <http://www.ncbi.nlm.nih.gov/nucest/EE109892?ordinalops=1&itool=EntrezSystem2.Pentrez.Sequence.Sequence_ResultsPanel.Sequence_RVDocSum>].

Berberoglu et al., "Radiation Characteristics of *Chlamydomonas reinhardtii* CC125 and its truncated chlorophyll antenna transformants tla1, tlaX, and tla1-CW+, " International Journal of Hydrogen Energy, 2008, vol. 33, pp. 6467-6483.

Ghirardi et al., "Photochemical Apparatus Organization in the Thylakoid Membrane of *Hordeum vulgare* wild type and chlorophyll b-less chlorina f2 mutant," Biochimica et Biophysica Act (BBA)—Bioengergetics, vol. 851, Issue 3, Oct. 1986, pp. 331-339 (abstract only).

Steinitz et al., "A mutant of the cyanobacterium Plectonema boryanum resistant to photooxidation," Plant Science Letters, vol. 16, Issues 2-3, 1979, pp. 327-335 (abstract only).

Koller et al., "Light Intensity During Leaf Growth Affects Chlorophyll Concentration and CO2 Assimilation of a Soybean Chlorophyll Mutant," Crop Science, 1974, vol. 14, pp. 779-782 (abstract only).

Shikanai et al., "Identification and Characterization of *Arabidopsis* Mutants with Reduced Quenching of Chlorophyll Fluorescence," Plant and Cell Physiology, 1999, vol. 40, No. 11, pp. 1134-1142 (abstract only).

Andersen, "Algal Culturing Techniques," 2005, p. 208.

Ben-Amotz, Ami. "Large-Scale Open Algae Ponds," presented at the NREL-AFOSR Joint Workshop on Algal Oil for Get Fuel Production in Feb. 2008.

Ebeling et al., "Design and Operation of a Zero-Exchange Mixed-Cell Raceway Production System," 2nd Int'l Sustainable Marine Fish Culture Conference and Workshop, Oct. 2005.

Ebeling et al., "Mixed-Cell Raceway: Engineering Design Criteria, Construction, and Hydraulic Characterization," North American Journal of Aquaculture, 2005, 67: 193-201 (abstract only).

Labatut et al., "Hydrodynamics of a Large-Scale Mixed-Cell Raceway (MCR): Experimental Studies," Aquacultural Engineering vol. 37, Issue 2, Sep. 2007, pp. 132-143.

(56) References Cited

OTHER PUBLICATIONS

Kizilisoley et al., "Micro-Algae Growth Technology Systems," Presented by Selim Helacioglu, Soley Institute, 2008.
Kent BioEnergy, "Fish Farm Empties Its Ponds to Grow Algae for Biofuels," Apr. 17, 2009 (http://www-csgc.ucsd.edu/newsroom/newsreleases/2009/algaeforbiofuls.html).
Hoyt et al., "Waves on Water Jets," J. Fluid Mech., 1977, vol. 83, Part 1, pp. 119-127.
Dodd, "Elements of Pond Design and Construction," CRC Handbook of Microalgal Mass Culture, Richmond, ed., Boca Raton, FL.: CRC Press, 1986, pp. 265-283.
Mitra et al., "Optical Properties of Microalgae for Enhanced Biofuels Production," Optics Express, Dec. 2008, vol. 16, No. 26.
Rodolphi et al., "Microalgae for Oil: Strain Selection, Induction of a Lipid Synthesis and Outdoor Mass Cultivation in a Low-Cost Photobioreactor," Biotechnology and Bioengineering, 2008, vol. 102, No. 1, pp. 100-112.
International Search Report mailed Sep. 16, 2009 for Application No. PCT/US2009/004296, filed Jul. 24, 2009.
Written Opinion mailed Sep. 16, 2009 for Application No. PCT/US2009/004296, filed Jul. 24, 2009.
Office Action mailed Nov. 14, 2012 in China Patent Application No. 200980138072.X, filed Jul. 24, 2009.
Official Action mailed Jul. 10, 2012 in Mexico Patent Application No. MX/a/2011/000934, filed Jul. 24, 2009.
Official Action mailed Mar. 5, 2013 in Mexico Patent Application No. MX/a/2011/000934, filed Jul. 24, 2009.
Duarte et al., "Efectos del glifosato (GP) con énfasis en organismos acuá ticos," Colunbia Orinoquia, ISSN: 0121-3709 ed: Unillanosv. 7, fasc. 1-2, pp. 70-100, 2004.
Technical Card: Glyphosate, Document filed for the Pesticide Action Network and the Alternatives Thereof, for Latin America (RAP-AL)- Communications and Administration Office, Apr. 2008.
Department of Environment, Housing and Territorial Development Ministry, Resolution (1009), published Jun. 17, 2008.
International Search Report and Written Opinion of the International Searching Authority mailed May 3, 2010 for Application No. PCT/US2010/000346, filed Feb. 4, 2010.
Patent Examination Report No. 1 mailed Jan. 9, 2013 in Australia Patent Application 2010210982, filed Feb. 4, 2010.
First Office Action mailed Nov. 5, 2012 in China Patent Application No. 201080012755.3, filed Feb. 4, 2010.
Official Action mailed Sep. 17, 2012 in Mexico Patent Application No. MX/a/2011/008222, filed Feb. 4, 2010.
International Search Report and Written Opinion of the International Searching Authority mailed Aug. 30, 2010 for Application No. PCT/US2010/001731, filed Jun. 15, 2010.
First Office Action mailed Dec. 14, 2012 in China Patent Application No. 201080036170.5, filed Jun. 15, 2010.
International Search Report and Written Opinion of the International Searching Authority mailed Aug. 19, 2010 for Application No. PCT/US2010/001755, filed Jun. 16, 2010.
International Search Report and Written Opinion of the International Searching Authority mailed Jul. 31, 2012 for Application No. PCT/US2012/035290, filed Apr. 26, 2012.
International Search Report and Written Opinion of the International Searching Authority mailed Jul. 30, 2010 for Application No. PCT/US2010/001315, filed May 4, 2010.
First Office Action mailed Oct. 25, 2012 in China Patent Application No. 201080027531.X, filed May 4, 2010.
Extended European Search Report mailed Oct. 5, 2012 in European Patent Application 10772376.9, filed on May 4, 2010.

BACKWARD-FACING STEP

CROSS-REFERENCE TO RELATED APPLICATIONS

The present application is related to U.S. patent application Ser. No. 12/485,862 titled "Systems, Methods, and Media for Circulating Fluid in an Algae Cultivation Pond," filed on Jun. 16, 2009.

FIELD OF THE INVENTION

The present invention relates generally to the carbonation of fluids, and more particularly to the use of backward-facing steps for initiating the carbonation of fluid in an aquaculture, such as an algae cultivation pond.

BRIEF SUMMARY OF THE INVENTION

Provided herein are exemplary systems, methods and media for carbonation of fluid in an algae cultivation pond via the use of backward-facing steps. In a first aspect, a method for initiating carbonation of a fluid flow in an algae cultivation pond is disclosed. Fluid flow is initiated over a backward-facing step in the algae cultivation pond. A backflow region is generated in the fluid flow downstream of the backward-facing step. Carbon dioxide is provided to the backflow region.

In a second aspect, a system for initiating carbonation of a fluid flow in an algae cultivation pond is disclosed. The system includes a step forming a portion of a pond bed of an algae cultivation pond. The system further includes a gas diffuser coupled to the pond bed of the algae cultivation pond downstream of the step. The gas diffuser is configured to introduce carbon dioxide in gas form into the fluid flow.

In a third aspect, a system for initiating carbonation of fluid in an algae cultivation pond is disclosed. The system includes a step forming a portion of a pond bed of the algae cultivation pond. The system further includes a nozzle coupled to a pressurized fluid source a carbonation source, and the step. The nozzle is configured to generate a jet of carbonated fluid from the pressurized fluid source and the carbonation source.

In a fourth aspect, a system for initiating carbonation of fluid in an algae cultivation pond is disclosed. The system includes a step forming a portion of a pond bed of the algae cultivation pond. The system includes a carbonation input forming a portion of the pond bed of the algae cultivation pond downstream of the step. The carbonation input is configured to release carbon dioxide into the fluid flow. The system includes a pH sensor. The system includes a processor and a computer-readable storage medium having embodied thereon a program executable by the processor to perform a method for adjusting a concentration of carbon dioxide in the algae cultivation pond. The computer-readable storage medium is coupled to the processor. The processor executes instructions on the computer-readable storage medium to measure a pH associated with the fluid in the algae cultivation pond via the pH sensor and initiate the release of carbon dioxide from the carbonation input based on the measured pH.

The methods described herein may be performed via a set of instructions stored on storage media (e.g., computer readable media). The instructions may be retrieved and executed by a processor. Some examples of instructions include software, program code, and firmware. Some examples of storage media comprise memory devices and integrated circuits. The instructions are operational when executed by the processor to direct the processor to operate in accordance with embodiments of the present invention. Those skilled in the art are familiar with instructions, processor(s), and storage media.

DETAILED DESCRIPTION

Provided herein are exemplary systems, methods and media for providing carbon dioxide to fluid in an algae cultivation pond. The fluid in the algae cultivation pond, e.g., algae cultivation pond fluid, may provide dissolved nutrients and/or raw materials to algae suspended therein. For instance, algae cultivation pond fluid may be composed of a mixture of fresh water and seawater, nutrients to promote algae growth, dissolved gases, disinfectants, waste products, and the like. Algal uptake of carbon dioxide dissolved in the algae cultivation pond fluid may facilitate photosynthesis, resulting in the accumulation of products such as algal biomass, lipids, and oxygen. The algae cultivation pond may exploit the natural process of photosynthesis in order to produce algae for high-volume applications, such as the production of biofuels.

The systems, methods, and media disclosed herein make use of a step forming a portion of the algae cultivation pond bed in a channel of an algae cultivation pond. The step may be referred to as backward-facing since the depth of the algae cultivation pond increases immediately downstream of the step. The step as referred to in this disclosure may be a backward-facing step, a rearward-facing step, and/or a backstep.

Fluid flow incident to a backward facing step may undergo boundary layer separation. Some of the fluid flow maintains characteristics of fluid flow upstream to the step, for instance, bulk flow may be maintained in the original direction of fluid flow.

Separation of the boundary layer, however, may result in flow separation, which leads to substantially different mean (e.g., bulk flow) characteristics and turbulent flow characteristics. A portion of the fluid flow in the algae cultivation pond may flow in a reverse and/or alternate direction from the direction of bulk fluid motion in the algae cultivation pond. This flow may be referred to as a backflow, and a region in which such reverse flow may be observed in the algae cultivation pond may be referred to as a backflow region. The backflow region may be located immediately downstream of the backward-facing step. The backflow region as referred to in this disclosure may include, for instance a recirculation region, a closed flow loop, a separation bubble, a dynamic bubble, and/or the like. For the purposes of the present disclosure, the 'backflow region' is considered to be distinct and separate from bulk motion of fluid in the algae cultivation pond, and the corresponding behaviors that may be observed in the bulk flow, e.g., circulation.

The backflow may further contact a surface of the step, which may induce further forward movement of the backflow. Thus, fluid flow may be captured in a closed flow loop immediately downstream of the backward-facing step. Fluid from the bulk fluid flow may be exchanged with fluid from the backflow region. Therefore, the backflow region may include reverse flow due to the separation of the boundary layer, as well as the flow that results when the backflow contacts a surface of the step and is re-oriented in the direction of the bulk flow.

Due to the presence of the step, the flow in the backflow region may become unsteady as a result of unsteady periodic vortex shedding due to the presence of the step. The backflow region may therefore result in the formation of one or more coherent structures (also termed 'coherent vortices' herein) along the width of the channel downstream of the step. The coherent structure may be substantially elliptical in shape and measure, at its greatest diameter, approximately six times to eight times the height of the step. However, the coherent structure may be dynamic in that it contracts, expands, shifts location in any or all directions, or any combination thereof, based on variations in the bulk flow.

The backflow region may interface with the bulk flow via a dividing streamline in a dividing streamline region. The dividing streamline may form a portion of the boundary layer downstream of the backward-facing step. The region in which the dividing streamline interfaces the pond bed downstream of the backward-facing step may be referred to as a reattachment region of the boundary layer of the fluid flow.

The carbon dioxide consumed during algal photosynthesis may be introduced in the algae cultivation pond based on a location of a step in an algae cultivation pond. Carbon dioxide may be introduced in a region of the algae cultivation pond via one or carbonation inputs. Carbonation inputs may include, for instance, gas diffusers, venturi nozzles, and/or the like. Carbonation inputs may be placed in a variety of configurations (e.g., arrays) downstream of the step. In some embodiments, the carbonation inputs form a portion of the algae cultivation pond bed. The position of the carbonation inputs relative to the location of the step may be determined based on various parameters of the step, such as step height, flow characteristics (e.g. flow velocity), and/or the type of carbonation input. The carbonation inputs may be placed in various configurations in the channel, as is described more fully herein.

Additionally, the carbonation inputs may be coupled to the backward-facing step. The carbonation inputs coupled to the step may issue jets of carbonated fluid, which in some instances may entrain a co-flow of fluid in the algae cultivation pond. The jet entrainment may promote the diffusion and/or advection of carbon dioxide into the algae cultivation pond fluid, yielding a substantially homogeneous mixture downstream from the jets. The resultant flow associated with one or more jets, i.e. jet flow, may induce bulk movement of fluid in the algae cultivation pond, i.e. circulation, or pond flow.

Introducing carbon dioxide to algae cultivation pond fluid, i.e. carbonation, in conjunction with a step may present benefits. Increases in turbulent kinetic energy may result in a turbulent boundary layer at the algal cell and enhance the rate of mass transfer to algal cells, thereby enhancing the uptake of carbon dioxide, in addition to other nutrients. The presence of a backflow region may impede the development of undesirable concentration gradients in the algae cultivation pond fluid.

The separation of flow over the step may enhance the dissolution of carbon dioxide into the algae cultivation pond fluid. The separation of flow induces the formation of coherent structures, which are characterized by high magnitude of vorticity, consistent structure, and periodic nature. The breakdown of these coherent vortices into smaller eddies—fluctuations of fluid flow random in time and structure—may enhance mixing of algae cultivation pond fluid in the backflow region and even downstream of the backflow region. Such enhanced mixing promotes a higher level of carbon dioxide dissolution in the algae cultivation pond fluid, thereby reducing or even eliminating carbon dioxide dissipation into the surrounding environment.

Figure 1:
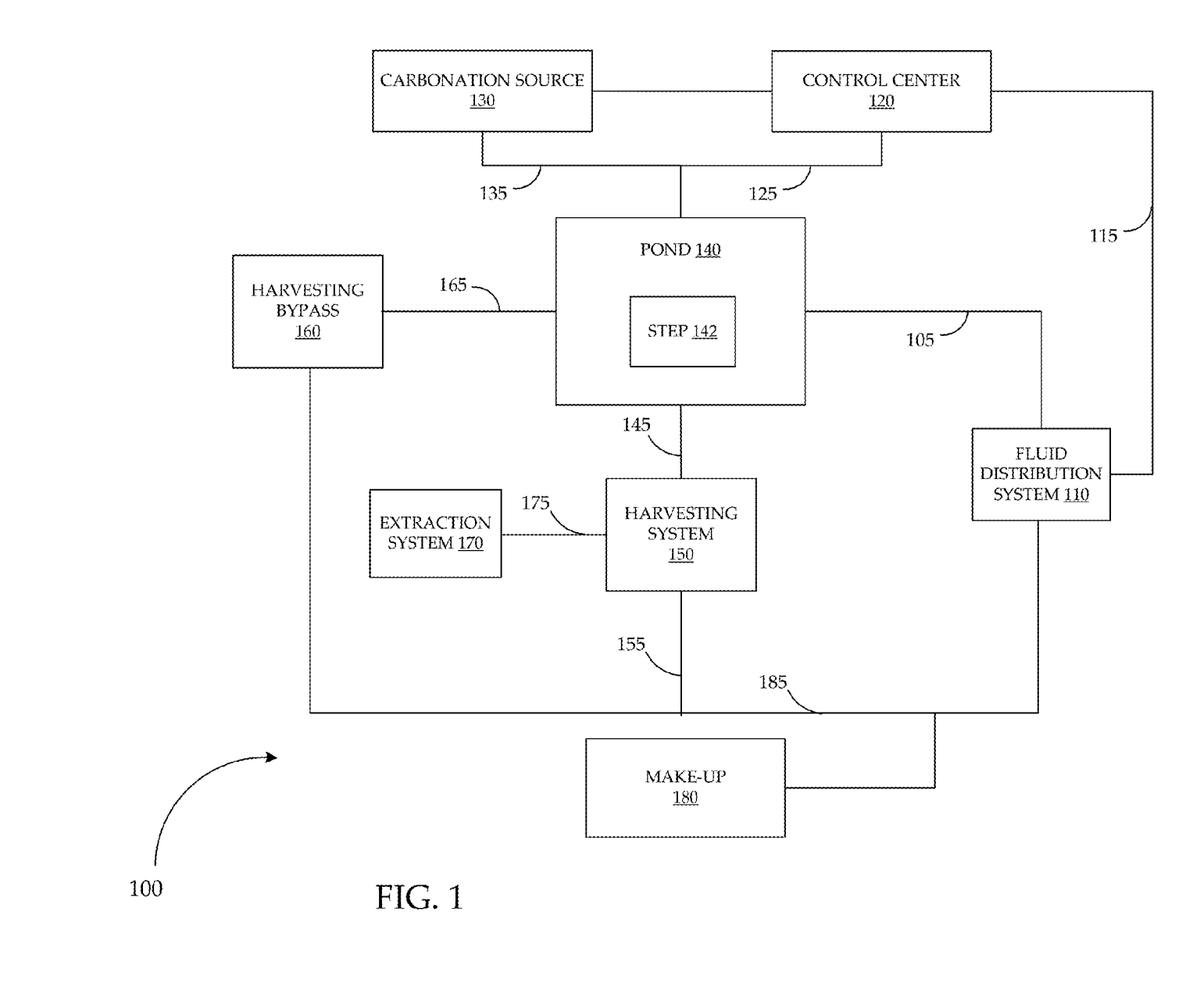
FIG. 1 is a block diagram of an exemplary pond circulation system in accordance with embodiments of the invention.

FIG. 1 is a block diagram of an exemplary pond carbonation system 100 including a backward-facing step. The pond carbonation system 100 includes a fluid distribution system 110, a control center 120, a carbonation source 130, a pond 140 including a step 142, a harvesting system 150, a harvesting bypass 160, an extraction system 170, and a make-up 180. The step 142 is located in the pond 140 and may form, for instance, a portion of a pond bed (not shown in FIG. 1). The step 142 and the pond 140 are discussed in further detail in the context of FIGS. 2-6. One skilled in the art will recognize that any number of items 110-180 may be present in the pond carbonation system 100. For instance, any number of steps 142 may be provided in a pond 140, and multiple ponds 140 may be provided in a pond carbonation system 100. For all figures mentioned herein, like numbered elements refer to like elements throughout.

The elements discussed herein may be coupled to one another via paths 105-185, and paths 105-185 represent exemplary relationships between elements 110-180 in the pond carbonation system 100. The paths may represent, for instance, electronic communication between elements. Additionally, the paths may represent physical paths, such as piping, among elements 110-180. Contents that may be transferred in the pond carbonation system 100 may include, for instance, algae cultivation pond fluid, algae suspension, water, carbon dioxide, algae biomass, or any combinations thereof. One skilled in the art will likewise recognize that the any number of paths 15-185 may be present in the pond carbonation system 100.

In some embodiments, fluid distribution system 110 may provide algae cultivation pond fluid to the pond 140 via the path 115. The fluid distribution system may introduce and/or initiate circulation in the algae cultivation pond 140 by initiating bulk fluid flow in one or more regions of the pond 140. These regions may be referred to as circulation regions of the pond 140. The bulk fluid flow generated in the circulation region may be sustained far downstream. Algae cultivation pond fluid may be introduced to the pond 140 via an intake (not shown in FIG. 1) from, for instance, the make-up 180 or for instance the pond 140, in a location downstream of the region in the pond 140 in which circulation is initiated.

The fluid distribution system 110 may include, for instance, a paddle wheel system, a jet circulation system, or any combinations thereof. The jet circulation system is detailed further in U.S. patent application Ser. No. 12/485,862. Components of the fluid distribution system 110 may be located in the pond 140, despite not being shown in FIG. 1. For instance, the fluid distribution system 110 may initiate bulk circulation of the algae cultivation pond fluid in the pond 140 using jets of pressurized algae cultivation pond fluid. Thus, the fluid distribution system 110 may include one or more nozzles configured to initiate via submerged jets, and these nozzles may be submerged in the pond 140.

Carbon dioxide is provided to the pond carbonation system 100 from the carbonation source 130. The carbonation source 130 may be, for instance, a power plant, a steel mill, a concrete mill, a byproduct of a chemical reaction, or any combination of these. The carbonation source 130 may provide pure carbon dioxide in gaseous form or a mixture of gases including carbon dioxide. Carbon dioxide may be provided to the pond 140 via path 135 as shown in FIG. 1. Upon introduction of the carbon dioxide to the algae cultivation pond fluid, the carbon dioxide may dissolve into solution. One skilled in the art will recognize that the path 135 may be of any length.

The pond carbonation system 100 may be used to cultivate algae for large volume applications, such as in the production of biofuels. The pond carbonation system 100 as such may be coupled to, for example, a harvesting system 150 and/or an extraction system 170. Algae may be harvested periodically from the pond 140. While harvesting is taking place, algae cultivation pond fluid may be routed from the pond 140 via a path 145. Upon harvesting, algae biomass may be routed to an extraction system 170 and algae cultivation pond fluid may be routed to the make-up 180 and/or the fluid distribution system 110 via paths 155 and 185 respectively. Alternatively, the algae cultivation pond fluid may be discarded (not shown in FIG. 1).

In order to maintain a desired level of algae cultivation pond fluid, a harvesting bypass 160 may be available in pond carbonation system 100. The harvesting bypass 160 may include an overflow component, which may act as a reservoir for surplus algae cultivation pond fluid (overflow component not shown in FIG. 1). The harvesting bypass 160 may be used to store excess algae cultivation pond fluid when harvesting is not taking place, such as during maintenance and repair, cleaning, or unfavorable weather conditions. In such scenarios, algae cultivation pond fluid may be routed via a path 165 to the harvesting bypass 160, and then via a path 185 to the fluid distribution system 110.

Components may be added to pond carbonation system 100 based on conditions that may play a role in algae cultivation and/or the needs of the particular genus or species of algae being cultivated. For instance, algae cultivation ponds having several acres of exposed surface area may lose large quantities of water via evaporation to the surrounding environment. Evaporation therefore may change concentrations of carbon dioxide, various nutrients and/or disinfectants in the algae cultivation pond fluid, and/or the pond temperature. In order to maintain desired concentrations of these nutrients and/or disinfectants, a make-up 180 may be available in pond carbonation system 100. The make-up 180 may introduce additional fresh water, seawater, disinfectants, and/or nutrients such as Aqua Ammonia, Phosphorous solutions, and trace metals, such as Co, Zn, Cu, Mn, Fe and Mo in appropriate concentrations. In some embodiments, the make-up 180 may draw fluid from the harvesting bypass 160 via the path 185.

The fluid distribution system 110, the carbonation source 130, the pond 140, the harvesting system 150, the harvesting bypass 160, the extraction system 170, and the make-up 180 may be coupled to, controlled by and/or otherwise monitored by the control center 120. The control center 120 may include any number of components, i.e. sensors, gauges, probes, control valves, servers, databases, clients, and any combination of these (not shown in FIG. 1 for simplicity). The sensors, servers, databases, clients and so forth may be communicative with one another via any number or type of networks, for example, LAN, WAN, Internet, mobile, and any other communication network that allows access to data, as well as any combination of these. Clients may include, for example, a desktop computer, a laptop computer, personal digital assistant, and/or any computing device. The control center 120 may monitor and/or measure various parameters in the pond 140, the carbonation source 130, and the fluid distribution system 110. These parameters include, but are not limited to pH, carbon dioxide concentration, head velocity, the head loss associated with the pond flow velocity, temperature, nutrient concentration, concentration of disinfectant(s), algal density, dissolved oxygen content, turbidity, and the like. The control center 120 may display and/or generate reports based on the various parameters measured in the pond 140.

In order to measure pH in the pond 140, the control center 120 may include a plurality of pH probes (not shown in FIG. 1), in communication with and controlled by the control center 120. The pH probes may be placed in any region of the pond 140, including for instance the backflow region and/or the region in which circulation is initiated. Such pH measurements may, for instance, be provided for display on a display device associated with the control center 120.

The control center 120 may store and/or execute software programs and/or instructions in order to take action based on the measured parameters. For instance, a software module associated with the control center 120 can be executed to compare measured parameters from the pond 140 to a desired set of parameters. If the measured parameters are not within a predetermined range of the desired set of parameters (e.g., within ten percent), the control center 120 can execute a software module (e.g., a software routine or code), to adjust the operation of any of the fluid distribution system 110, the pond 140, the harvesting system 150, the harvesting bypass 160, the extraction system 170, and the make-up 180 in order to bring the measured parameters within the predetermined ranges.

For instance, a desired set of parameters may be set by a user of the control center 120 (via user input). An exemplary pH range may be set by a user, for instance, between 7.4 to 8.0. If the measured pH is lower than 7.4, the control center 120 may automatically provide instructions to the carbonation source 130 to discontinue providing carbon dioxide to the pond 140. Additionally, the control center 120 may provide instructions to the fluid distribution system 110 to and increase the intake of algae cultivation pond fluid from make-up 180 until the measured pH is in line with the predefined parameters. Alternatively, if the measured pH is found to be higher than 8.0, then the control center 120 may automatically provide carbon dioxide to the pond 140.

Figure 2:
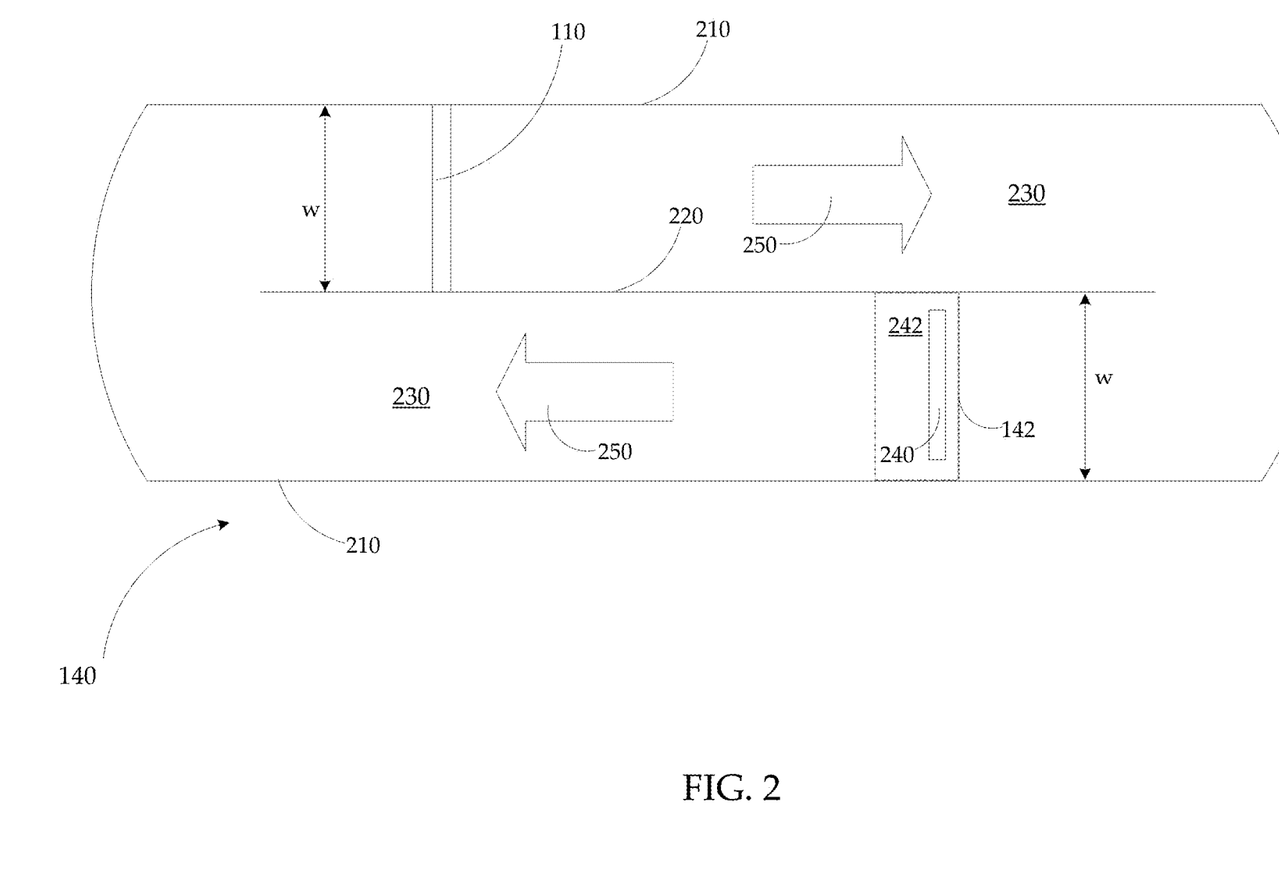
FIG. 2 is a top view of an exemplary algae cultivation pond as described in the context of FIG. 1.

FIG. 2 is a top view of an exemplary algae cultivation pond, such as pond 140 described in the context of FIG. 1. Although the example illustrated in FIG. 2 conforms to an open-air raceway pond design, one skilled in the art will recognize that the disclosure herein may be adapted to other pond designs, for instance single channels, flumes, and the like. The algae cultivation pond may be filled with algae cultivation pond fluid to any depth in the algae cultivation pond.

The pond 140 includes an outer wall 210 and divider 220, forming two channels 230 on either side of the divider 220. In some embodiments, the divider 220 may be located in the center of the pond 140, forming channels of substantially equal width in the pond 140. Alternatively, the divider 220 may be located off-center such that one of the two channels 230 is wider. The pond 140 may include one or more step regions 242 including one or more steps 142. A step 142 may be constructed along the width and/or along a portion of the width of the pond bed as indicated in FIG. 2 and may be coupled to the pond bed.

The pond 140 includes one or more steps 142. A step 142 may form a portion of the pond bed (shown in FIG. 3) and may measure between five and thirty-five entimeters in height. The height of the step 142 may be measured in relation to the corresponding increase in depth of the pond in the step region 242. The height of the step 142 may influence fluid flow in the step region 242, and is further discussed in the context of FIGS. 3-6. Bulk flow of algae cultivation pond fluid is represented in pond 140 by arrows 250, which indicate the direction of bulk flow in the channels 230.

As shown in FIG. 2, one or more components of the fluid distribution system 110 may be included in the pond 140. For instance, fluid distribution system 110 may include a series of paddle wheels, which can be used to initiate fluid flow in the pond 140. Similarly, a jet circulation system as referred to above may be used, and nozzles associated with the jet circulation system may be submerged in the algae cultivation pond fluid in the pond 140.

Fluid flow in the step region 242, upon being incident to a step 142, may undergo flow separation. While a portion of the fluid flow may maintain characteristics of the bulk fluid flow upstream of the step region 242, a portion of the bulk fluid may flow in a reverse and/or alter direction from the direction of bulk fluid motion in the algae cultivation pond. The portion of flow which may reverse and/or change direction may be referred to as a backflow, is discussed further in the context of FIGS. 3-6.

A carbonation input 240 may be located immediately downstream of the step 142. Carbonation inputs 240 may be coupled to one or more carbonation sources, such as the carbonation source 130 discussed in the context of FIG. 1. In some embodiments, carbonation inputs 240 substantially span the width of the pond bed as shown in FIG. 2. Carbonation inputs 240 may include, for instance, gas diffusers, venturi nozzles, and any combinations of these. Any number of carbonation inputs 240 may be positioned in the step region 242. For instance, the carbonation inputs 240 may be coupled to the pond bed in a fixed array. Alternatively, the position of the carbonation input 240 may be variable and form a dynamic array that may be modified based on measured conditions in the pond 140. The position of the carbonation input 240 may be determined based on predefined parameters and controlled by execution of a software module by the control center 120 (software module not shown in FIG. 2).

Figure 3:
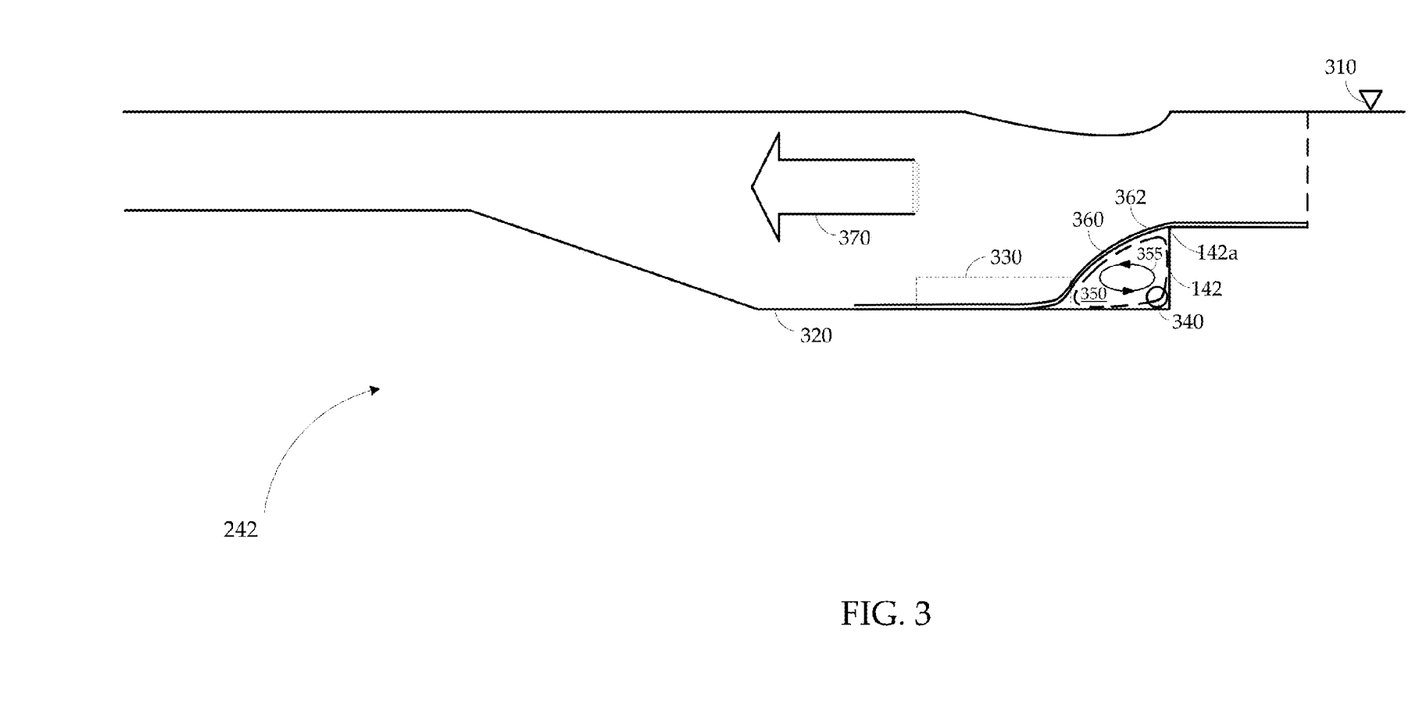
FIG. 3 illustrates a side view of an exemplary step region in an algae cultivation pond described in the context of FIGS. 1 and 2.

FIG. 3 illustrates an embodiment of the step region 242 as described in the context of FIGS. 1 and 2. Shown in FIG. 3 is a side view cross section of a channel 230 in the pond 140. The step region 242, as discussed earlier, may form a portion of a channel 230 as discussed in the context of FIG. 2 and may include the step 142 in addition to a portion of the fluid flow downstream of the step 142. The step 142 may be additionally referred to as a backward-facing step, a backstep, and/or a rearward-facing step 142, since depth of the pond is increased immediately downstream of the step 142. Depth may be characterized, for instance, as a distance between a pond bed 320 and a surface of fluid in the algae cultivation pond, as indicated by surface level marker 310. The pond may be filled to any depth with algae cultivation pond fluid.

Presence of the step 142 in the pond 140 initiates flow separation in the bulk flow. As mentioned earlier, when the flow is incident to the step 142, boundary layer separation may occur, thereby inducing flow separation. A portion of the flow immediately downstream of the step may possess characteristics of the bulk flow upstream of the step. This flow is represented in FIG. 3 by streamlines 360 and 362 and the arrow 370, which indicates the direction of bulk flow of algae cultivation pond fluid in the channel 230.

A portion of the flow immediately downstream of the step may reverse or otherwise proceed in a direction alternate to the bulk flow (e.g., in a direction contrary to that indicated by the arrow 370). This reverse flow, indicated by the streamline 355, may form a backflow region 350 which is represented by the dashed line shown in FIG. 3. The backflow region 350, may interface with the bulk flow (as represented by the arrow 370), in the vicinity of the streamline 360, which may be referred to as a dividing streamline and/or dividing streamline region 360. The dividing streamline 360 may interface with the pond bed 320 in a reattachment region 330, which corresponds to the reattachment of the boundary layer. As such, the reattachment region 330 may be understood as a boundary for the backflow region 350. Algae cultivation pond fluid may still, however, be exchanged between the bulk flow (represented by the streamlines 360 and 362) and flow in the backflow region 350 (represented by the streamline 355).

The backflow region 350 may form a region that is distinct from the bulk flow along the step 142 and/or across the width of the channel 230. Contact of the bulk flow with the tip 142a of the step 142 generates a velocity gradient and high Reynolds stress in the vicinity of the tip 142a. The high Reynolds stresses correspond to the production of turbulence in the vicinity of the step 142, and sustained turbulent flow downstream of the step 142.

The bulk fluid flow and the backflow downstream of the step 142 are dynamic and unsteady processes (e.g., not steady with respect to time). Thus, the size and position of the backflow region 350 may change with time, despite being represented by a time-averaged profile and position. For instance, the backflow region 350 may contract or expand, alter in shape, and/or drift spatially in any direction with respect to the time-averaged profile and/or position. Since the backflow region 350 may be dynamic in nature, the time-averaged position and/or profile of the reattachment region 330 may vary in accordance with variations in the backflow region 350.

FIG. 3 is a side view of step region 242 and illustrates a carbonation configuration in accordance with embodiments of the invention disclosed herein. In FIG. 3, the step 142 incorporates the use of a gas diffuser 340 as a carbonation input 240, as such, the gas diffuser 340 may be coupled to the carbonation source 130. Carbon dioxide (in gas form) may be received from the carbonation source 130 (as shown in FIG. 1) and released into the backflow region 350 (dashed line indicating an exemplary time-averaged position and profile).

Any number of the gas diffusers 340 may be positioned in various configurations in the step region 242. For instance, the gas diffusers 340 may be organized in an array forming a portion of the pond bed 320 along the width of the channel 230. Alternatively, the gas diffusers 340 may be coupled to the pond bed 320 in a dynamic array which may be controlled by execution of software modules at the control center 120 (as discussed in the context of FIG. 1). The positions of the gas diffusers 340 may be adjusted in relation to one another as well as in relation to the step region 242 based on, for instance flow characteristics (e.g., flow velocity, flow rate), which may be measured and/or otherwise determined at the control center 120.

Further, any amount and concentration of carbon dioxide may be provided to the backflow region 350 by the gas diffuser 340. For instance, carbon dioxide may be released in gas form from the gas diffuser 340 at a rate of approximately 2.2 to 2.9 standard cubic feet per hour per meter of a channel width associated the backflow region 350. The channel width, for instance, may be determined based on the characteristics of the channel 230 as disclosed in the context of FIG. 2.

Upon release of carbon dioxide into the backflow region 350, the carbon dioxide is dissolved into solution. Any carbon dioxide that remains in gas form may be captured by the closed flow loop of the backflow region 350. The turbulence generated in the bulk flow by the backflow region 350 increases the rate of mass transfer of carbon dioxide to the algae cultivation pond fluid, thereby maximizing the efficiency associated with the dissolution of carbon dioxide and minimizing the loss of carbon dioxide to the surrounding environment.

Figure 4:
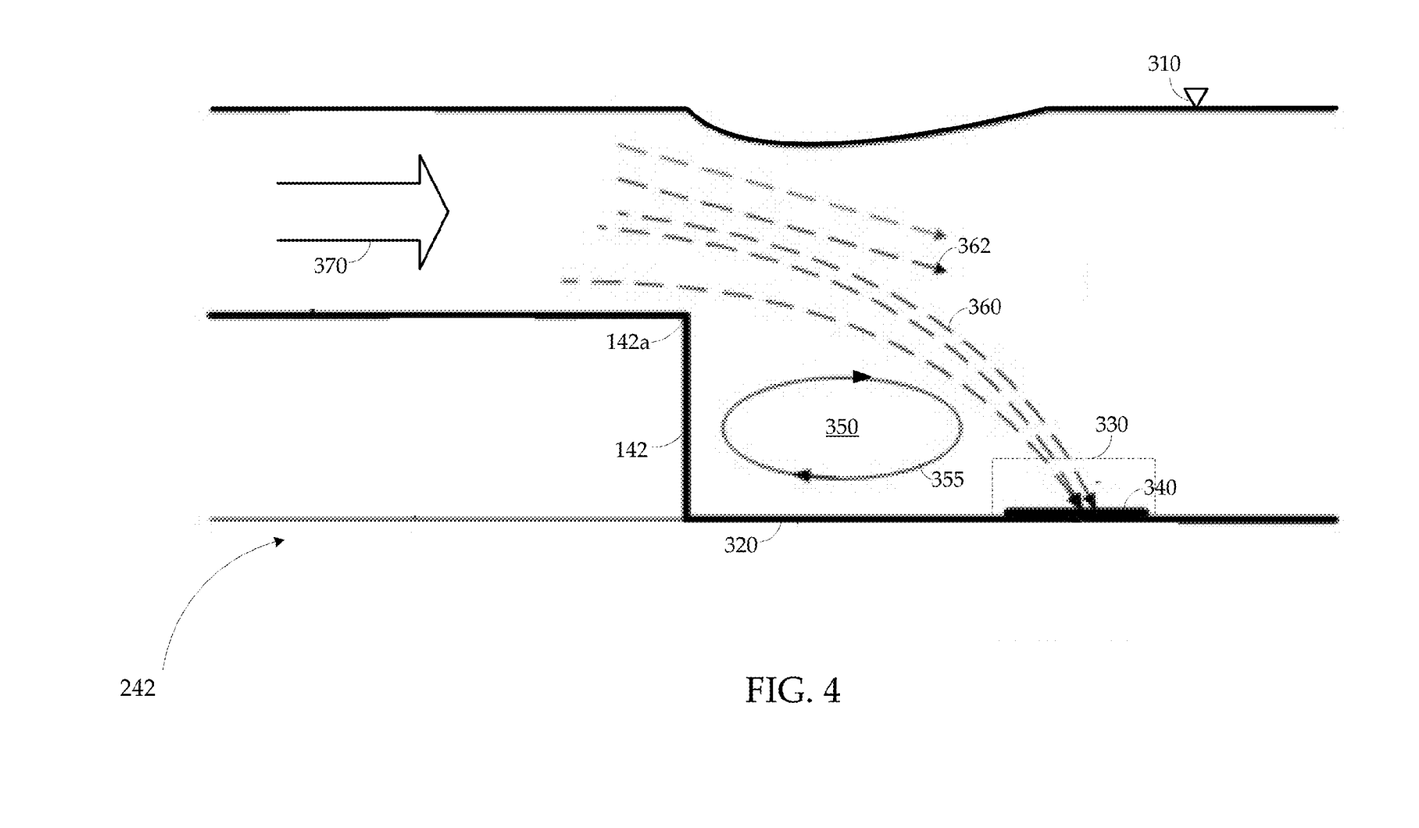
FIG. 4 illustrates a side-view of an exemplary step region as described in the context of FIGS. 1 and 2.
Figure 5:
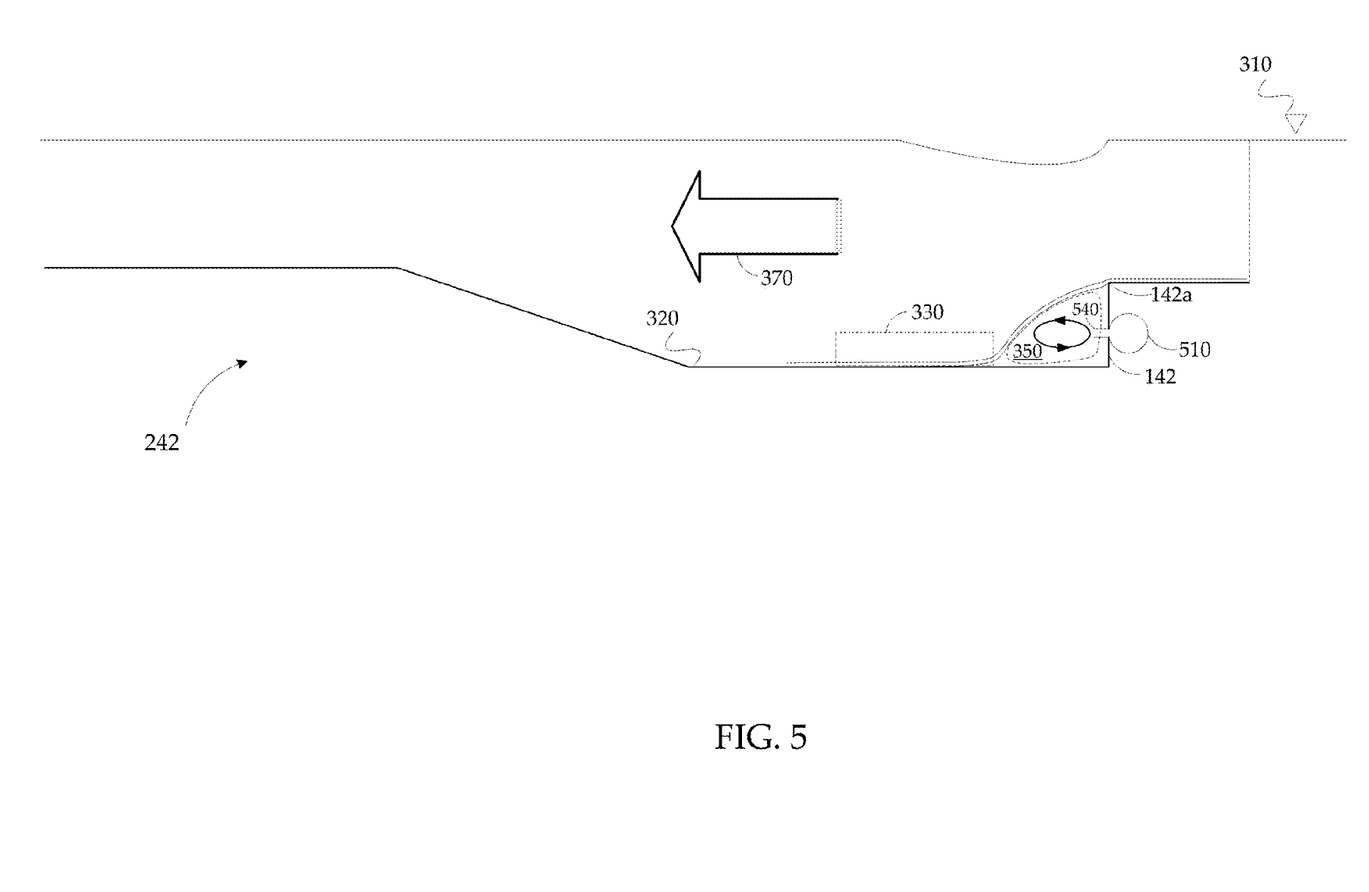
FIG. 5 illustrates a side-view of an exemplary step region as described in the context of FIGS. 1 and 2.

FIGS. 4 and 5 illustrate embodiments of the step region 242 as described in the context of FIGS. 1 and 2. In FIG. 4, the gas diffuser 340 may be positioned in a reattachment region 330 of a boundary layer associated with the bulk flow (indicated by arrow 370). The turbulence associated with fluid flow in the reattachment region 330 may increase the mass transfer rate of carbon dioxide, and, by enhancing surface area of contact, enhances the dissolution efficiency of the carbon dioxide.

In the embodiment illustrated in FIG. 5, a nozzle 540 may be coupled to a manifold 510, which in turn is coupled to the step 142. The nozzle 540 may discharge a jet of carbonated fluid into the pond 140. The jet of carbonated fluid may be generated from pressurized algae cultivation pond fluid and dissolved carbon dioxide in solution, and form a portion of the fluid distribution system 110. The jet of carbonated fluid may entrain the fluid in the algae cultivation pond, thereby initiating circulation of the bulk flow of algae cultivation pond fluid in the pond 140. Further, carbon dioxide may be distributed via diffusion and/or advection into the bulk flow of the algae cultivation pond fluid. As such, the nozzle 540 may be oriented such that the jet of carbonated fluid is discharged in the direction of bulk flow (as indicated by the arrow 370). Alternatively, the nozzle may be oriented such that the jet of carbonated fluid is discharged at an angle to the direction of bulk flow, further described in the context of FIG. 6.

The height of the step may determine characteristics of the backflow region 350, such as a time-averaged position of the backflow region 350, time-averaged profile of the backflow region 350, and the like. The height of the step may also determine the location of the reattachment region 330 of the boundary layer. In some embodiments, the approximate location of the reattachment region 330 as measured downstream from the step 142 may be determined by the following relation:

location of reattachment region≈step height*n where n is a dimensionless constant ranging between approximately 5 to approximately 10.

The configurations of carbonation inputs 240 in the step region 242 may exploit the conditions generated by the step 142 in the pond 140. The height of the step 142 may play a significant role in determining positions for carbonation inputs 240 that enhance carbonation efficiency and minimize loss of carbon dioxide into the surroundings. For instance, carbonation inputs 240 may be positioned such that carbon dioxide is provided directly to the backflow region 350. Alternatively, carbonation inputs 240 may be positioned such that carbon dioxide is provided to the bulk flow of algae cultivation pond fluid as described in the context of FIG. 6 or in the reattachment region 330, as described in the context of FIG. 4.

The control center 120 may measure carbon dioxide concentrations in any of the aforementioned regions in the step region 242. In some embodiments, the control center 120 may execute a software module to simulate the pH profile of the algae cultivation pond fluid using as inputs, for instance, the height of the step 142, flow characteristics of the algae cultivation pond fluid (e.g., flow velocity, flow rate), and initial carbon dioxide concentrations. The control center 120 may then determine the mean position of the backflow region 350, the mean profile of the backflow region 350, the reattachment region 330 and/or the mean position of the dividing streamline 360 (e.g. a dividing streamline region) and provide carbon dioxide accordingly.

Figure 6:
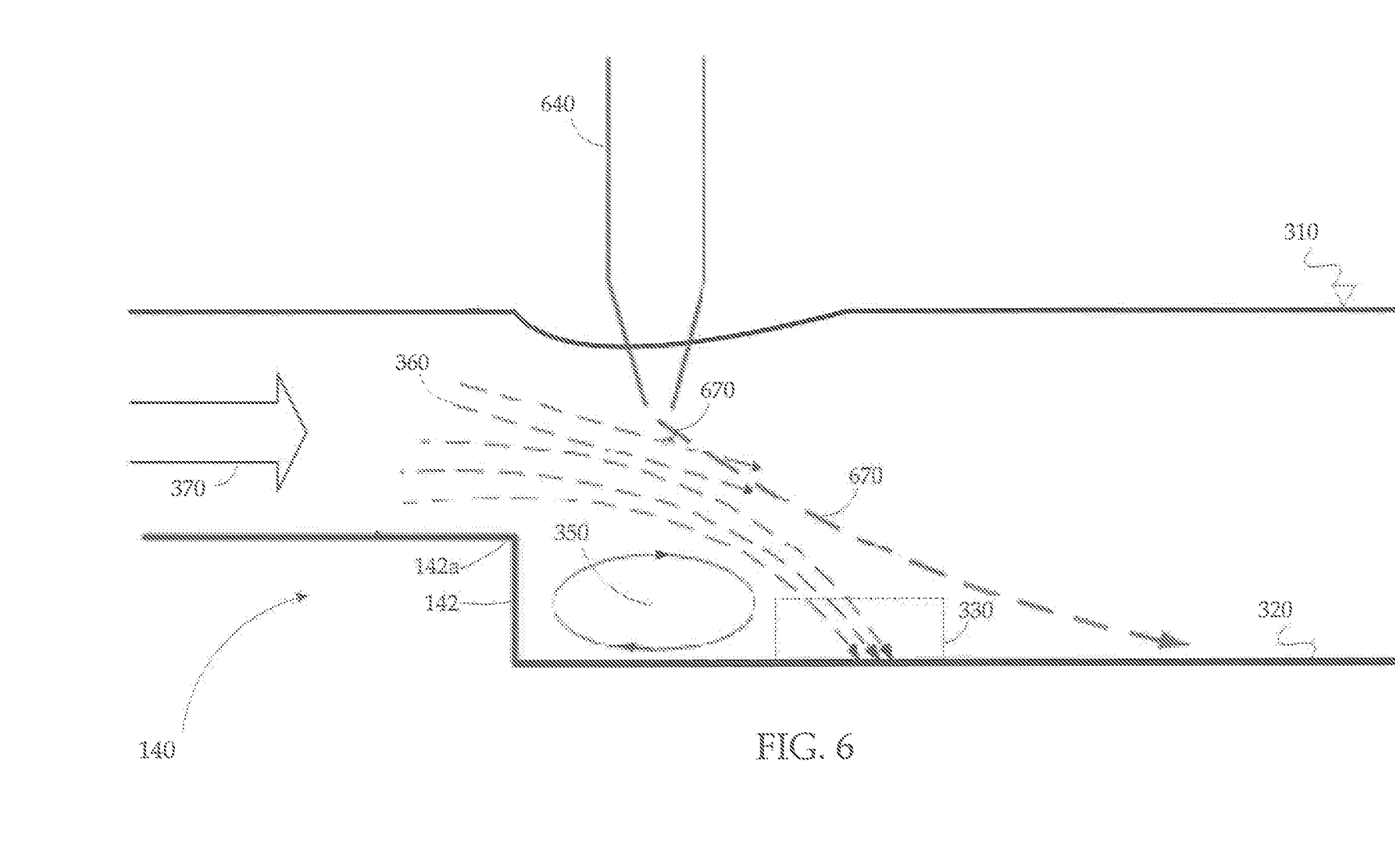
FIG. 6 illustrates a side-view of an exemplary step region as described in the context of FIGS. 1 and 2.

FIG. 6 is a side view of step region 242 and illustrates as described in the context of FIG. 3. In FIG. 6, the step region 242 incorporates the use of a nozzle 640 as the carbonation input 240. Any number of nozzles 640 may be included, despite only one shown in FIG. 6, and the nozzles 640 may be organized in an array. For instance, the nozzles 640 may form a longitudinal array across the width of a channel, for instance the channel 230. The nozzles 640 may be coupled to the carbonation source 130 (disclosed in the context of FIG. 1). The nozzles 640 may introduce a mixture of fluids (including carbon dioxide) to algae cultivation pond fluid in backflow region 350.

The nozzles 640 may also provide carbon dioxide in solution to the step region 242. For instance, carbon dioxide may be mixed with algae cultivation pond fluid at the carbonation source 130. The algae cultivation pond fluid may be received from one of the harvesting system 150, the harvesting bypass 160, the make-up 180, or any combination thereof (path not shown in FIG. 1). Alternatively, carbon dioxide may be mixed with algae cultivation pond fluid in a portion of the path 135. The carbon dioxide may then be fully dissolved as the fluid is transported to the path 135, upon injection into the pond 140.

Various parameters corresponding to the nozzle 640 may be controlled, adjusted, and/or otherwise manipulated at the control center 120 by execution of a software module. Parameters that may be controlled include, but are not limited to nozzle position, frequency of nozzle discharge, location of discharge, direction and/or angle of discharge (e.g., discharge directed upstream or downstream). The nozzle 640 may be configured to discharge in the backflow region 350. In some embodiments, these parameters may be manipulated by user input to the control center 120.

As shown in FIG. 6, the nozzle 640 may be configured to discharge in the vicinity of a dividing streamline 360, as indicated by bubble path 670. When flow is incident on a backward-facing step, flow which is initially substantially laminar may become turbulent and accelerate in the vicinity of the step. As such, providing carbon dioxide in gas form, in solution, or any combination thereof, in the vicinity of a dividing streamline 360 (e.g., in a dividing streamline region 360) may allow certain benefits. Upon discharge into the algae cultivation pond fluid, any carbon dioxide remaining in gas form (e.g., along the bubble path 670) may, due to the turbulence generated from the presence of the step 142, be fully dissolved into solution. The turbulence generated in the bulk flow by the backflow region 350 may increase the rate of mass transfer the carbon dioxide in the algae cultivation pond fluid, thereby maximizing the efficiency associated with the dissolution of carbon dioxide and minimizing the loss of carbon dioxide to the surrounding environment.

Pure carbon dioxide was provided to the algae cultivation pond in experiments conducted by the inventors. In a first experiment, the pure carbon dioxide was introduced to the algae cultivation pond fluid by venturi nozzles in a ratio of approximately 200 mg of pure carbon dioxide per gallon of algae cultivation pond fluid. The mixture was then introduced into the pond which resulted in no loss of carbon dioxide to atmosphere. In a second experiment, pure carbon dioxide was provided by a diffuser at a rate of approximately 2.2 to approximately 2.9 standard cubic feet per hour per meter of a channel width associated with the backflow region.

Figure 7:
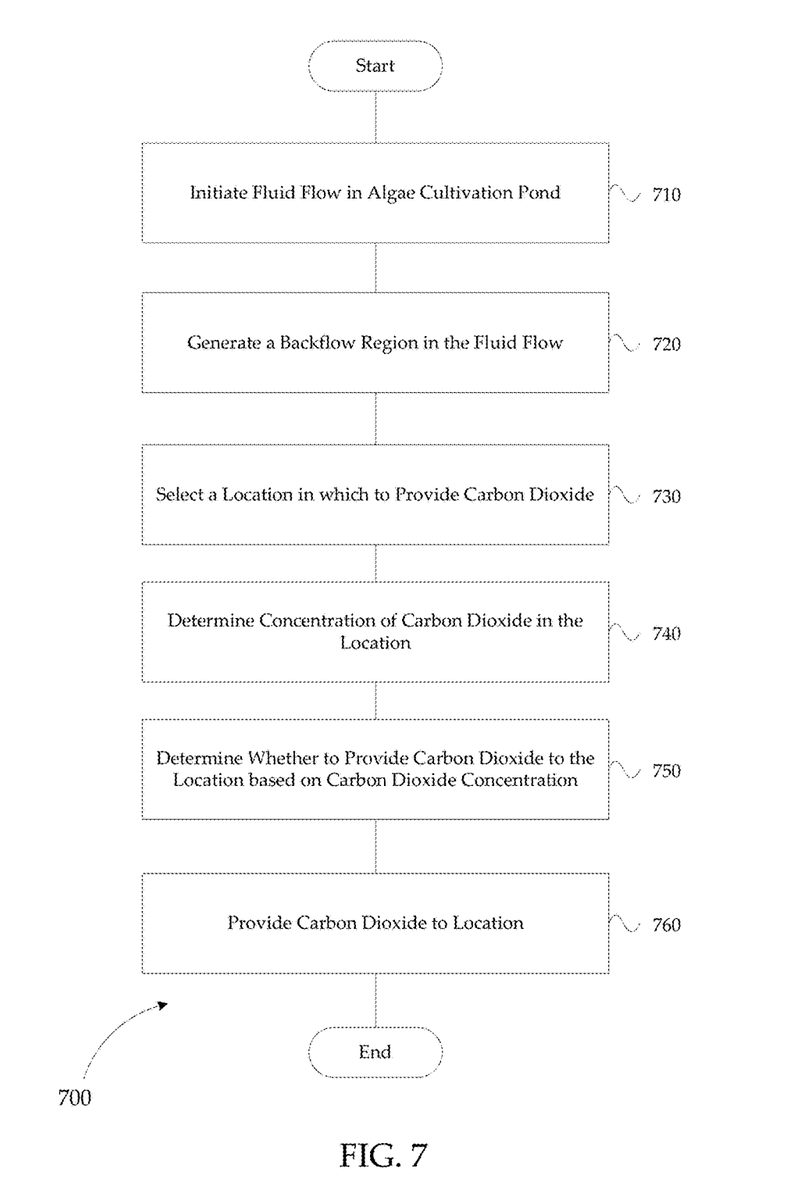
FIG. 7 is a flow chart of an exemplary method 700 for initiating carbonation in an algae cultivation pond.

FIG. 7 is a flow chart of an exemplary method 700 for initiating carbonation in an algae cultivation pond. The method 700 may be practiced in the pond carbonation system 100 via one or more components disclosed in the context of FIG. 1. The method 700 may involve one or more computer-implemented steps executable by one or more modules by the control center 120. Further, the method 700 may be implemented in any of the embodiments disclosed in the context of FIGS. 2-6.

In step 710, fluid flow is generated in an algae cultivation pond. Fluid flow may be generated, for instance, by the fluid distribution system 110 in the pond 140. As mentioned earlier, the fluid distribution system 110 may include, for instance, a paddle wheel and/or a jet circulation system as disclosed in the context of U.S. patent application Ser. No. 12/485,862. Various components of the fluid distribution system 110 may be present in the pond 140 in order to generate fluid flow.

In step 720, a backflow region is generated in the fluid flow. The backflow region 350 as shown in FIGS. 3-6 is exemplary in this regard, in that the backflow region 350 may be generated when fluid flow is incident on a step 142. In some embodiments, the backflow region 350 may be sustained indefinitely so long as fluid flow is generated in the pond 140 by the fluid distribution system 110.

In step 730, a location in which to measure carbon dioxide is selected. Step 730 may, for instance, be selected by the control center 120 upon execution of a software module. The software module may determine, for instance, a mean position region in the backflow region 350 in the fluid flow, as indicated by the dashed line in FIG. 3. The control center 120 may then select whether to provide the carbon dioxide to the backflow region 350, the reattachment region 330, and/or a region proximate to the dividing streamline 360 based on the dynamics of the backflow region 350.

In step 740, a concentration of carbon dioxide in the selected location may be determined. Step 740 may be conducted by, for instance, the control center 120 via execution of a software module configured to receive data from a pH sensor in the pond 140. In some embodiments, the control center 120 may provide measurements corresponding to carbon dioxide concentration for display on a display device associated with the control center 120. Alternatively, the control center 120 may generate a report and/or generate a log event in a database associated with the control center 120.

In step 750, a determination as to whether further carbon dioxide should be provided to the location may be made. Step 750 may be conducted by the control center 120. For instance, the control center 120, via execution of a software program, may determine whether the measurements from the pH sensor correspond to acceptable carbon dioxide concentrations for the selected region.

If the carbon dioxide concentration is determined in step 750 to be outside of acceptable ranges, then the control center 120 may transmit instructions to the carbonation source 130 to discontinue providing carbon dioxide to the algae cultivation pond fluid. Alternatively, if the carbon dioxide concentration determined in step 750 is determined to be within acceptable ranges, further carbon dioxide may be provided to the algae cultivation pond fluid in step 760 via the carbonation inputs 240.

The above-described functions and/or methods may include instructions that are stored on storage media. The instructions can be retrieved and executed by a processor. Some examples of instructions are software, program code, and firmware. Some examples of storage media are memory devices, tapes, disks, integrated circuits, and servers. The instructions are operational when executed by the processor to direct the processor to operate in accord with the invention. Those skilled in the art are familiar with instructions, processor(s), and storage media. Exemplary storage media in accordance with embodiments of the invention are discussed in the context of, for example, the control center 120 of FIG. 1. In addition, portions of the method 700 may be embodied in code that is executable by a computer associated with the control center 120.

Figure 8:
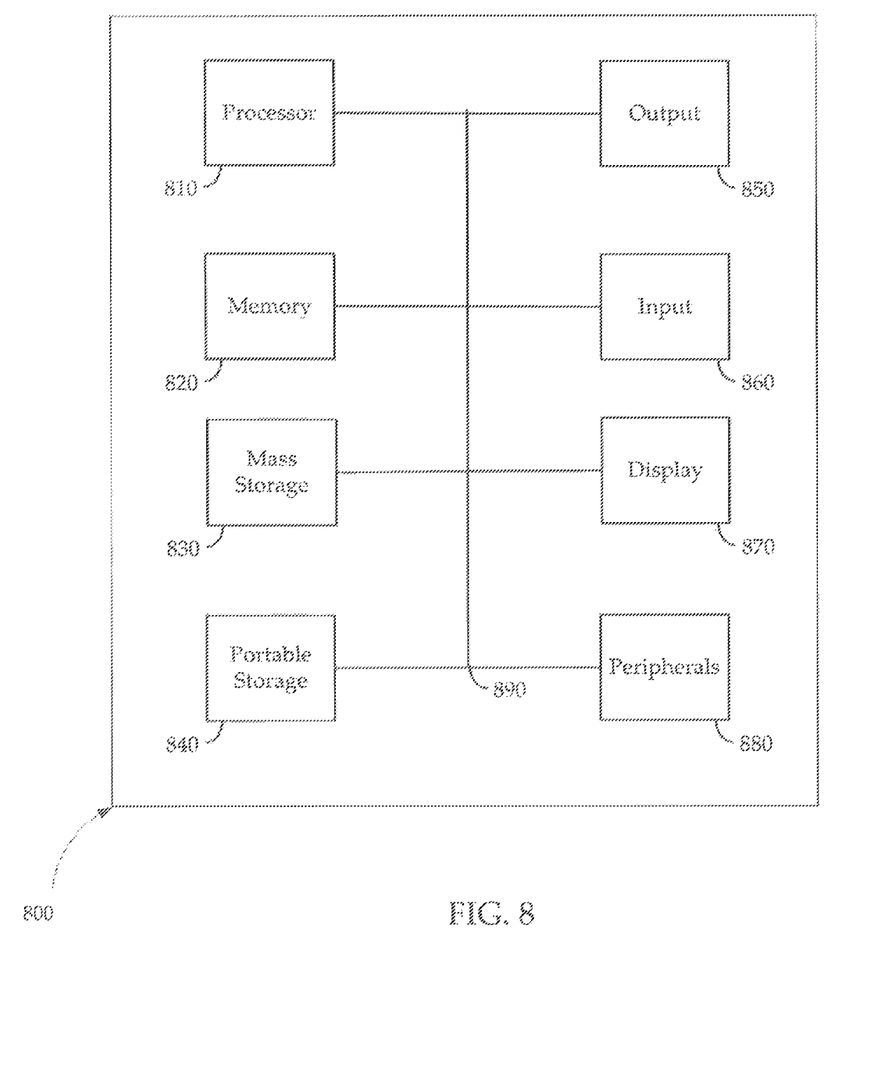
FIG. 8 is a block diagram of an exemplary computing environment in accordance with embodiments of the present invention.

FIG. 8 is a block diagram of an exemplary computing device for initiating carbonation in an algae cultivation pond, e.g., the pond 140, in accordance with embodiments of the present invention. In some embodiments, the exemplary computing device of FIG. 8 can be used to implement the control center 120.

The computing system 800 of FIG. 8 includes one or more processors 810 and main memory 820. Main memory 820 stores, in part, instructions and data for execution by processor 810. Main memory 820 can store the executable code when in operation. The computing system 800 of FIG. 8 further includes a mass storage device 830, a portable storage device 840, output devices 850, user input devices 860, a display system 870, and peripheral devices 880.

The components shown in FIG. 8 are depicted as being connected via a single bus 890. However, the components can be connected through one or more data transport means. For example, processor 810 and main memory 820 can be connected via a local microprocessor bus, and the mass storage device 830, peripheral device(s) 880, portable storage device 840, and display system 870 can be connected via one or more input/output (I/O) buses.

Mass storage device 830, which can be implemented with a magnetic disk drive or an optical disk drive, is a non-volatile storage device for storing data and instructions for use by processor 810. Mass storage device 830 can store the system software for implementing embodiments of the present invention for purposes of loading that software into main memory 820.

Portable storage device 840 operates in conjunction with a portable non-volatile storage medium, such as a floppy disk, compact disk or Digital video disc, to input and output data and code to and from the computing system 800 of FIG. 8. The system software for implementing embodiments of the present invention can be stored on such a portable medium and input to the computing system 800 via the portable storage device 840.

Input devices 860 provide a portion of a user interface. Input devices 860 may include an alpha-numeric keypad, such as a keyboard, for inputting alpha-numeric and other information, or a pointing device, such as a mouse, a trackball, stylus, or cursor direction keys. Additionally, the computing system 800 as shown in FIG. 8 includes output devices 850. Examples of suitable output devices include speakers, printers, network interfaces, and monitors.

Display system 870 may include a CRT, a liquid crystal display (LCD) or other suitable display device. Display system 870 receives textual and graphical information, and processes the information for output to the display device.

Peripheral devices 880 may include any type of computer support device to add additional functionality to the computer system. For example, peripheral device(s) 880 may include a modem or a router.

The components contained in the computing system 800 of FIG. 8 are those typically found in computer systems that can be suitable for use with embodiments of the present invention and are intended to represent a broad category of such computer components that are well known in the art. Thus, the computing system 800 of FIG. 8 can be a personal computer, hand held computing device, telephone, mobile computing device, workstation, server, minicomputer, mainframe computer, or any other computing device. The computer can also include different bus configurations, networked platforms, multi-processor platforms, etc. Various operating systems can be used including Unix, Linux, Windows, Macintosh OS, Palm OS, and other suitable operating systems.

Upon reading this paper, it will become apparent to one skilled in the art that various modifications may be made to the systems, methods, and media disclosed herein without departing from the scope of the disclosure. As such, this disclosure is not to be interpreted in a limiting sense but as a basis for support of the appended claims.

What is claimed is:

1. A method for initiating carbonation of a fluid flow in an algae cultivation pond, the method comprising:

initiating fluid flow over a backward-facing step in the algae cultivation pond;

generating a backflow region in the fluid flow downstream of the backward-facing step; and providing carbon dioxide to the backflow region.

2. The method of claim 1, wherein the backflow region corresponds to a closed flow loop.

3. The method of claim 1, wherein the backflow region interfaces a dividing streamline.

4. The method of claim 1, wherein the backflow region is bounded by a reattachment region of a boundary layer associated with the backflow region.

5. The method of claim 4, wherein providing carbon dioxide to the backflow region includes providing carbon dioxide in the reattachment region.

6. The method of claim 1, wherein the carbon dioxide is provided to the backflow region at a rate ranging from approximately 2.2 to approximately 2.9 standard cubic feet per hour per meter of a channel width associated with the backflow region.

* * * * *

UNITED STATES PATENT AND TRADEMARK OFFICE
CERTIFICATE OF CORRECTION

PATENT NO. : 8,748,160 B2  
APPLICATION NO. : 12/631567  
DATED : June 10, 2014  
INVENTOR(S) : Mehran Parsheh et al.

Page 1 of 1

It is certified that error appears in the above-identified patent and that said Letters Patent is hereby corrected as shown below:

On the title page, item (73)  
Assignee's name should be: "Aurora Algae, Inc."

Signed and Sealed this  
Thirtieth Day of September, 2014

Michelle K. Lee  
*Deputy Director of the United States Patent and Trademark Office*